United States Patent
Bergey et al.

(10) Patent No.: US 6,902,335 B2
(45) Date of Patent: Jun. 7, 2005

(54) HAND HELD DISPENSING AND APPLICATION APPARATUS

(75) Inventors: Michael S. Bergey, Washington Crossing, PA (US); Bruce Detwiler, Spring City, PA (US); James L. Hussey, Holland, OH (US); Kurt Koptis, Yucca Valley, CA (US); Yelena Lipoveskaya, Howell, MI (US); Mahmood Mohiuddin, Hawthorn Woods, IL (US)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 0 days.

(21) Appl. No.: 10/431,769

(22) Filed: May 8, 2003

(65) Prior Publication Data

US 2004/0223802 A1 Nov. 11, 2004

(51) Int. Cl.⁷ .............................. B43K 5/14; B43K 5/00
(52) U.S. Cl. ....................................... 401/132; 401/205
(58) Field of Search ................................ 401/132, 133, 401/134, 135, 196, 205; 604/3

(56) References Cited

U.S. PATENT DOCUMENTS

| | | |
|---|---|---|
| 416,388 A | 12/1889 | Wiley |
| 3,429,429 A | 2/1969 | Poitras ........................ 206/47 |
| 3,647,305 A | 3/1972 | Baker et al. .................... 401/7 |
| 4,084,910 A | 4/1978 | LaRosa ....................... 401/133 |
| 4,127,339 A | 11/1978 | Malacheski et al. ........ 401/132 |
| 4,427,115 A | 1/1984 | Laipply ...................... 206/484 |
| 4,430,013 A | 2/1984 | Kaufman .................... 401/132 |
| 4,629,080 A | 12/1986 | Carveth ........................ 215/11 |
| 4,643,725 A | 2/1987 | Schlesser et al. ........... 604/306 |
| 4,648,506 A | 3/1987 | Campbell .................... 206/216 |
| 4,696,393 A | 9/1987 | Laipply ....................... 206/210 |
| 4,805,767 A | 2/1989 | Newman ..................... 206/219 |
| 4,812,067 A * | 3/1989 | Brown et al. ................ 401/132 |
| 4,871,091 A | 10/1989 | Preziosi ......................... 222/92 |
| 4,896,768 A | 1/1990 | Anderson .................... 206/210 |
| 4,921,137 A | 5/1990 | Heijenga ..................... 222/107 |
| 5,287,961 A | 2/1994 | Herran ........................ 206/219 |
| D351,338 S | 10/1994 | Koptis ......................... D9/302 |
| D363,377 S | 10/1995 | Koptis ......................... D4/122 |
| 5,487,932 A | 1/1996 | Dunshee ....................... 428/68 |
| 5,490,736 A * | 2/1996 | Haber et al. ............ 401/132 X |
| D369,976 S | 5/1996 | Koptis ......................... D4/114 |
| 5,558,874 A | 9/1996 | Haber et al. ................. 424/402 |
| 5,577,851 A | 11/1996 | Koptis ......................... 401/202 |
| D385,789 S | 11/1997 | Koptis ......................... D9/436 |
| D386,853 S | 11/1997 | Koptis ......................... D32/45 |
| D386,854 S | 11/1997 | Koptis ......................... D32/45 |
| D386,855 S | 11/1997 | Koptis ......................... D32/45 |

(Continued)

FOREIGN PATENT DOCUMENTS

FR 2 506 140 11/1982

Primary Examiner—David J. Walczak
(74) Attorney, Agent, or Firm—Donald O. Nickey

(57) ABSTRACT

A dispensing and application apparatus designed to contain pre-measured amounts of a flowable substance. The apparatus comprises a compartment 130 for storing the substance that is partially enclosed by a frangible seal 210, an applicator 100, and an expandable chamber 170 designed to accept and dissipate the hydraulic force created when pressure is applied to the compartment 130, rupturing the frangible seal 210, and expelling the substance into the chamber 170. The applicator 100 is attached to the chamber 170 with an applicator bond area 180. The expandability of the chamber 170 is conferred by expandability of the applicator 100, and is varied in different embodiments by altering the ratio between the area of the applicator bond area 180 and the area of the applicator 100. The frangible seal 210, in one of many embodiments, may be a chevron shape stress riser 250 with a point of inflection 260 oriented towards the compartment 130. A removable cap may cover the applicator.

39 Claims, 7 Drawing Sheets

U.S. PATENT DOCUMENTS

| | | | |
|---|---|---|---|
| D387,563 S | 12/1997 | Koptis | D4/114 |
| D398,235 S | 9/1998 | Koptis | D9/448 |
| 6,007,264 A | 12/1999 | Koptis | 401/132 |
| D418,303 S | 1/2000 | Koptis | D4/114 |
| 6,099,184 A | 8/2000 | Koptis | 401/190 |
| 6,105,761 A | 8/2000 | Peuker et al. | 206/229 |
| 6,117,123 A | 9/2000 | Barney et al. | 604/410 |
| D433,235 S | 11/2000 | Koptis | D4/114 |
| 6,536,974 B2 * | 3/2003 | Redmond | 401/133 |
| 6,547,063 B1 * | 4/2003 | Zaveri et al. | 206/219 |
| 6,547,468 B2 * | 4/2003 | Gruenbacher et al. | 401/133 |

\* cited by examiner

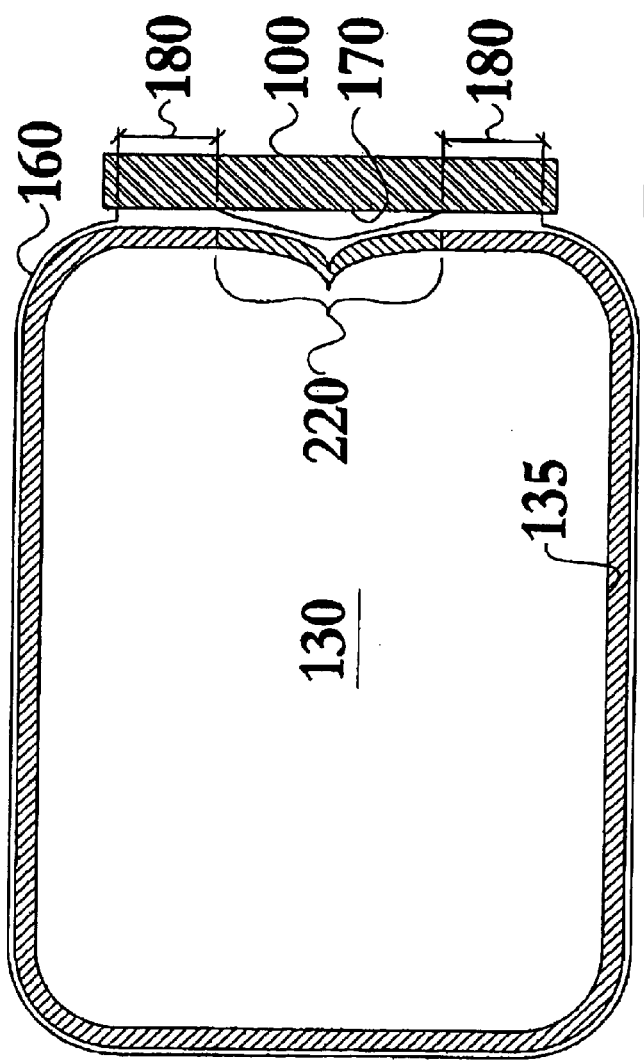
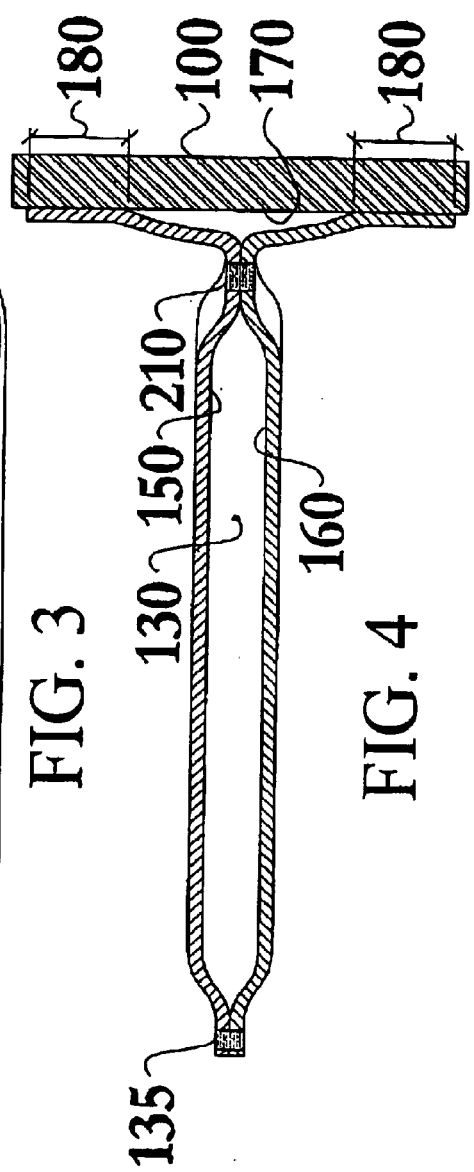
FIG. 3
FIG. 4

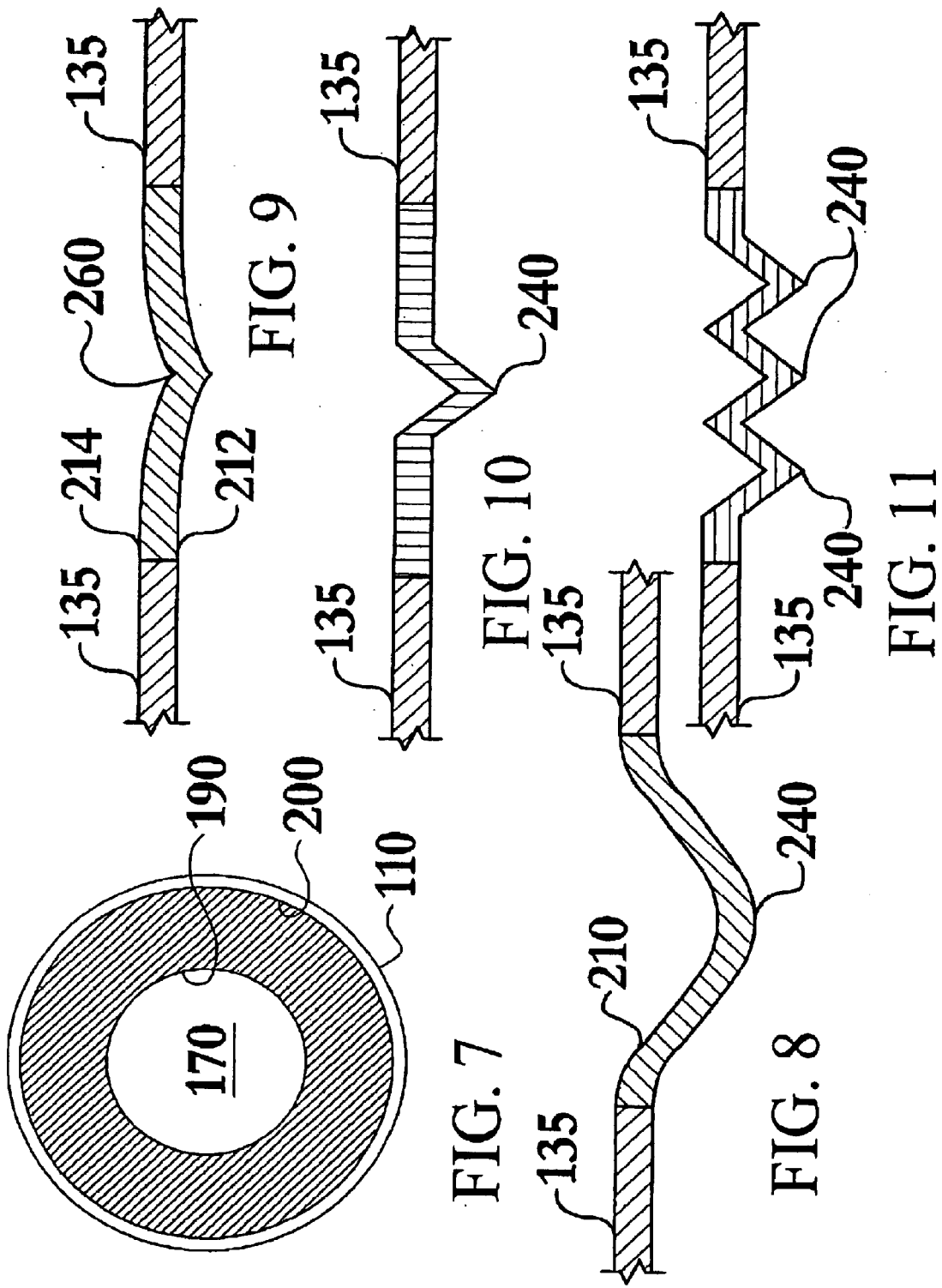

HAND HELD DISPENSING AND APPLICATION APPARATUS

TECHNICAL FIELD

The instant invention relates to hand held dispensing packages, and particularly to a flexible package for storing and dispensing a fluid substance, wherein a controlled rupture seal facilitates transfer of the substance into an unsealed area behind a foam applicator at the time of dispensing. The integral foam applicator facilitates a clean and even spreading of the dispensed substance.

BACKGROUND OF THE INVENTION

Measured amounts of various fluid substances are increasingly commonly dispensed in relatively small flexible packages often composed of plastic or foil. The fluids include a wide variety of products, including foodstuffs such as condiments (for example ketchup, mustard, relish and the like), personal care products such as shampoos and skin creams, cleaning products such as various packaged "wipes," and pharmaceutical products such as medications.

A typical example is the ubiquitous single serving ketchup pack, which is generally formed of two sheets of foil or plastic, superimposed over one another and then sealed together around the periphery, with a notch or other means to facilitate tearing one edge away from the container. The user tears open the container, dispenses the condiment, and then disposes of the package.

Such packaging, while relatively simple and inexpensive, poses numerous drawbacks in this most simple embodiment. Firstly, the simplest such package contains no integral means for directing or spreading the dispensed fluid. In particular, thick fluids tend to be dispensed as a bolus, leaving the user to find an implement to spread the bolus, or otherwise to improvise with the possibly unsanitary outside of the now empty package to form a crude spreader. Alternatively, thin fluids tend to be dispensed in a difficult to control stream.

Second, the package can be quite difficult to open, particularly for those with arthritic hands or otherwise compromised grip strength. This difficulty is at least in part caused by the fact that, in the simplest conventional embodiments of this package, it is necessary to tear away one of the sidewalls of the packaging in order to release the contents. Such a sidewall must be relatively strong in order to contain the contents under normal handling conditions, which may include accidental compression. Even a small amount of moisture or skin oil on the surface of the packaging can make gripping and tearing the generally small package nearly impossible. It is extremely common to see frustrated users of such packaging using their teeth to open ostensibly manually "tear open" packages. Such a technique poses obvious aesthetic and hygienic issues.

Third, velocity of the fluid as it is expelled from the packaging varies with viscosity of the fluid, the amount of sidewall opened and the pressure applied. Anyone who has squeezed a ketchup package with only a pinpoint opening in its side can testify to the extreme distances the condiment can be propelled.

Various attempts have been made over the years to address these problems, with varying degrees of success. The creation of packaged, pre-moistened towelettes facilitates spreading but requires a handling of the dispensed contents. Pre-loaded, disposable, swabs obviate handling, but contain very small amounts of dispensable liquid. The need to facilitate spreading a dispensed liquid was addressed by means of an integral roller in U.S. Pat. No. 5,577,851 to Koptis. The '851 patent teaches a sponge applicator attached to a tube dispenser that contains a quantity of a substance, such as painter's spackle, to be dispensed. After use, the sponge applicator is designed to be removed, cleaned, and returned to the tube dispenser. The reuse of the sponge applicator raises issues of potential hardening and chemical or bacterial deterioration of the sponge. This makes the '851 applicator unsuitable for use with products such as those intended for human consumption, where bacterial contamination may be devastating. Such problems can be overcome with single use, or "throw away" sponge applicators, but the complexity of the '851 device makes it ineffective on a cost basis for single use containers.

A similar attempt to provide an integral spreader is seen in U.S. Pat. No. D363,377, which provides a roller atop a dispensing container. The roller spreads the dispensed fluid, but is subject to the same cleaning and hygienic drawbacks posed by the sponge pad applicator of the '851 patent.

Efforts to produce an integral spreading means suitable for single use containers have exhibited mixed success. For example, U.S. Pat. No. 6,007,264 to Koptis teaches a variation on the simplest form of packaging, that of two superimposed sheets sealed together around their periphery, with the provision of peelable flaps along one edge of the package. The user peels back the flaps, pulling apart one sealed edge of the package and thus exposing the contents. The peeled back flaps, at an approximate 90-degree angle to the package, thereby provide a butterfly wing type spreader for spreading the contents. Such a design overcomes any need to clean or re-use the spreading device, as the entire unit is disposable.

However, the utility of the '264 design has been found to be directly proportional to the viscosity of the fluid dispensed. For example, fluids with a high viscosity, such as ketchup or heavy creams, tend to be dispensed as a discrete bolus, whereupon they can be effectively smeared about the intended surface by the butterfly wings. However, experience has shown that liquids of low fluid viscosity, such as some pharmaceutical preparations and other relatively thin liquids, tend to be dispensed from the opened container in a stream, as opposed to a bolus, and run out of the flap or wing spreading area before they can be effectively spread.

The '264 device attempts to counter this propensity by disclosing an embodiment wherein an absorbent foam applicator is either applied in two pieces to the opposing flaps or is applied in a single piece bridging the flaps. Such embodiments are designed to provide an absorbent surface area to facilitate the spreading of the fluid dispensed. However, experience with the base design has revealed that it is marginally effective for this purpose. In practice, separate foam applicators that do not bridge the container opening may increase surface area and absorbency for spreading, but do nothing to retard the sudden flow of material from the ruptured packaging. Even in the embodiment wherein the absorbent pad bridges the opening, practice has shown that when the pouch is squeezed and the frangible seal breaks, the contents of the pouch burst through the seal and the liquid tends to squirt through the absorbent pad, rather than being gently absorbed into the pad as intended.

As to the second problem, that of facilitating the opening of the container, various methods have been proposed. The '264 device provides enlarged tear flaps that are intended to facilitate gripping the container, however, the problem of tearing away a relatively strong sidewall of the container remains. In essence the present invention is directed to improvements for the Koptis '264 device and all teaching contained in U.S. Pat. No. 6,007,264 are herein incorporated by reference.

In U.S. Pat. No. 4,921,137 to Heijenga, the container is equipped with an enlarged ear-like structure that facilitates grip. In addition, the '137 device contains, within the ear-like structure, a preformed channel portion that attempts to address the third problem, that of dependably producing a large enough egress channel for the dispensed material so as to minimize excessive pressure effects, such as uncontrolled squirting of the contents. However, the '137 device makes no provision to address the problem of spreading a bolus of dispensed liquid.

U.S. Pat. No. 6,117,123 to Barney discloses a flexible container that provides for the storage and mixing together of diluents and medicaments. The container incorporates multiple compartments, separated by preferentially peelable seals, in which the diluents and medicaments are stored. The peelable seals are ruptured by manipulation of the container to thereby mix the components together for delivery through standard I.V. equipment to a patient. The seals are constructed such that the seal between the diluent and medicament compartments is preferentially ruptured such that a liquid medicament and a diluent are always mixed before the combined solution is accessible for administration.

The prior art fails to disclose a disposable, unit dose container for liquids of varying viscosity that allows for easy opening, without touching the container contents, where the liquid is dispensed into an unsealed area behind the foam pad in such a manner that the liquid is easily dispensed. Such a dispensing pouch must be inexpensive and easy to manufacture, maintain the integrity of the liquid until dispensing, and must reliably dispense the liquid without being unduly susceptible to accidental release, yet be easy to open. Further, the absorbent pad may be protected by a cover that can be easily removed just prior to dispensing, and the design of the pad should facilitate easy and even spreading of the container contents.

SUMMARY OF THE INVENTION

The instant invention provides a novel dispensing apparatus that addresses the shortcomings of the prior art. In its most general design, the apparatus comprises a compartment, a chamber, and an applicator pad. The chamber and the compartment may be fabricated out of separate materials that are bonded together. It is preferred, however, that the chamber and the compartment be fabricated of the same material as a single structure separated into two sections by a frangible seal.

The present invention is designed to contain a flowable substance that can be dispensed by applying pressure upon the compartment area, where the substance is stored. The pressure ruptures the frangible seal and expresses the substance into the chamber, behind the applicator. The expansion of the chamber walls and the resilience of the applicator pad allows the substance to spread out behind and into the applicator, where it is available to be expelled and applied.

The prior art describes the concept of an applicator attached to flexible foil wings of a dispensing package, but experimentation with such a design revealed that it was deficient in any number of applications. When sufficient pressure is exerted behind a seal of a closed compartment, the seal ruptures and the material behind the seal is expelled through the seal, releasing the pressure to the atmosphere. The force with which the material flows through the ruptured seal depends on many factors, including but not limited to the viscosity of the fluid, the amount of pressure applied, and the surface area, or orifice area, of the rupture in the seal.

Experimentation with the general design of the package of U.S. Pat. No. 6,007,264 to Koptis, while sufficient in some applications, showed a number of shortcomings. First, if the applicator foam was attached as separate pads (opposing pads disposed on the underside of outwardly folding wings) there was a tendency for the dispensed substance to break through the frangible seal and squirt out on the user or floor, before it could be absorbed and spread by the absorbent pads. It was noted that the severity of this problem increased with increased pressure, decreased area or orifice of seal rupture, and decreased viscosity of the substance dispensed. Alternatively, when the absorbent pad was designed as a single pad spanning a small central opening in the packaging seal, the problem remained unattenuated, as the dispensed substance tended to shoot through the absorbent pad, with the same ill effects noted above.

The instant invention achieves controlled dispensing and application by the combination of two essential features. First, it has a controlled rupture seal that reliably ruptures at a predetermined pressure with a sufficient orifice size, to prevent extremely high pressure dispensing. Second the apparatus features a relatively expandable expansion chamber that absorbs the hydraulic shock of the dispensed substance, providing it time for the fluid to spread into the applicator.

Experimentation with various designs of frangible seals revealed that various possible designs achieved at least some degree of success. For example, the frangible seal could be a straight frangible seal fabricated to be thinner, or to be less securely heat-sealed, than the primary seal. In a second design, the frangible seal with a stress riser was oriented away from the pressure and provided good results. However, in the preferred embodiment, a frangible seal with a chevron shaped stress riser with the point of maximum inflection oriented towards the pressure, was found to present optimal characteristics in terms of breaking reliability and adequate seal rupture area.

Even with an optimally designed frangible seal, it was realized that an expansion chamber was needed to contain the dispensed substance at a reasonably low pressure while it was being absorbed into the applicator pad. It was found that a chamber formed by partially adhering the foam applicator pad to the wings of the device was useful in absorbing the hydraulic shock of the dispensed substance breaking through the frangible seal. However, it was also observed that the sizing of the chamber played an important role in the efficacy of the chamber concept. If the applicator pad were attached over a relatively large area to the wings of the package, it creates a relatively small chamber and is unable to cushion the aforementioned hydraulic shock. In contrast, if the applicator pad were attached over a very small area of the applicator wings of the package, there would be a relatively large expansive chamber available to cushion the hydraulic force, and there might be insufficient force to move the substance into and through the applicator pad.

The apparatus according to the invention may also have a removable cap for the applicator pad, which depending on the exact design and characteristics of the cap, can maintain cleanliness, or even sterility, of the applicator pad. The apparatus offers a low cost disposable packaging for a wide array of flowable substances, which can include, by way of example and not limitation; pharmaceutical antiseptics, salves, cosmetics, ointments and creams. Additionally, the apparatus provides a package that offers convenience in storage, resistance to package breakage, better sanitation, and lower spillage or waste. In addition, the inventive apparatus provides packaging that allows a user to apply a small measured quantity of a substance in a controlled manner without getting it on the fingers or hands and without the necessity of using the fingers, hands or an additional implement to spread the substance. The ability to easily apply the dispensed substance without direct hand contact with the substance improves aesthetic and hygienic concerns during application, and avoids contamination of the substance as it is dispensed.

BRIEF DESCRIPTION OF THE DRAWINGS

Without limiting the scope of the present invention as claimed below and referring now to the drawings and figures:

FIG. 3 shows a top plan view of a second (interior) surface of the apparatus shown in FIG. 1 taken along section line 3—3 of FIG. 1 wherein the top layer of FIG. 1 has been removed and reveals the chevron frangible seal;

FIG. 4 shows a cross section view of the apparatus shown in FIG. 1 taken along section line 4—4 of FIG. 1;

FIG. 7 shows a cross section view of the apparatus shown in FIG. 1 taken along section line 7—7 of FIG. 1;

FIG. 8 shows a top plan view of a variation of the frangible seal;

FIG. 9 shows a top plan view of a variation of the frangible seal;

FIG. 10 shows a top plan view of yet another variation of the frangible seal;

FIG. 11 shows a top plan view of another variation of the frangible seal;

DETAILED DESCRIPTION OF THE INVENTION

Thus, there is disclosed a dispensing and application apparatus wherein the apparatus is designed to contain a flowable substance, the apparatus comprising: 1) a compartment; 2) at least one sheet divided by at least one seal to form the compartment, wherein one of the at least one seals is a frangible seal designed to break when exposed to a predetermined pressure, thereby creating a channel permitting fluid communication between the compartment and a chamber; 3) an applicator having a periphery and being joined to the at least one sheet with at least one applicator bond; and 4) the chamber being formed by the at least one sheet, and the applicator, and bounded in part by the applicator, the at least one applicator bond, and the frangible seal.

There is further disclosed a means for dispensing and applying a fluid comprising: 1) a means for storing the fluid; 2) at least one means for establishing a boundary divided by at least one joining means to form the means for storing the fluid, wherein one of the at least one joining means is a means for establishing fluid communication between the storing means and a means for expansion when exposed to a predetermined pressure; 3) a means for applying the fluid joined to the at least one boundary establishing means with at least one means for bonding; and 4) the expansion means being formed by the at least one boundary establishing means, and the applying means, and bounded in part by the applying means, the at least one bonding means, and the fluid communication establishing means.

The dispensing and application apparatus of the instant invention presents a significant advance in the state of the art. The preferred embodiments of the apparatus accomplish this by new and novel arrangements of elements that are configured in unique and novel ways and which demonstrate previously unavailable but desirable characteristics.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention as set forth in the claims.

Figure 1:
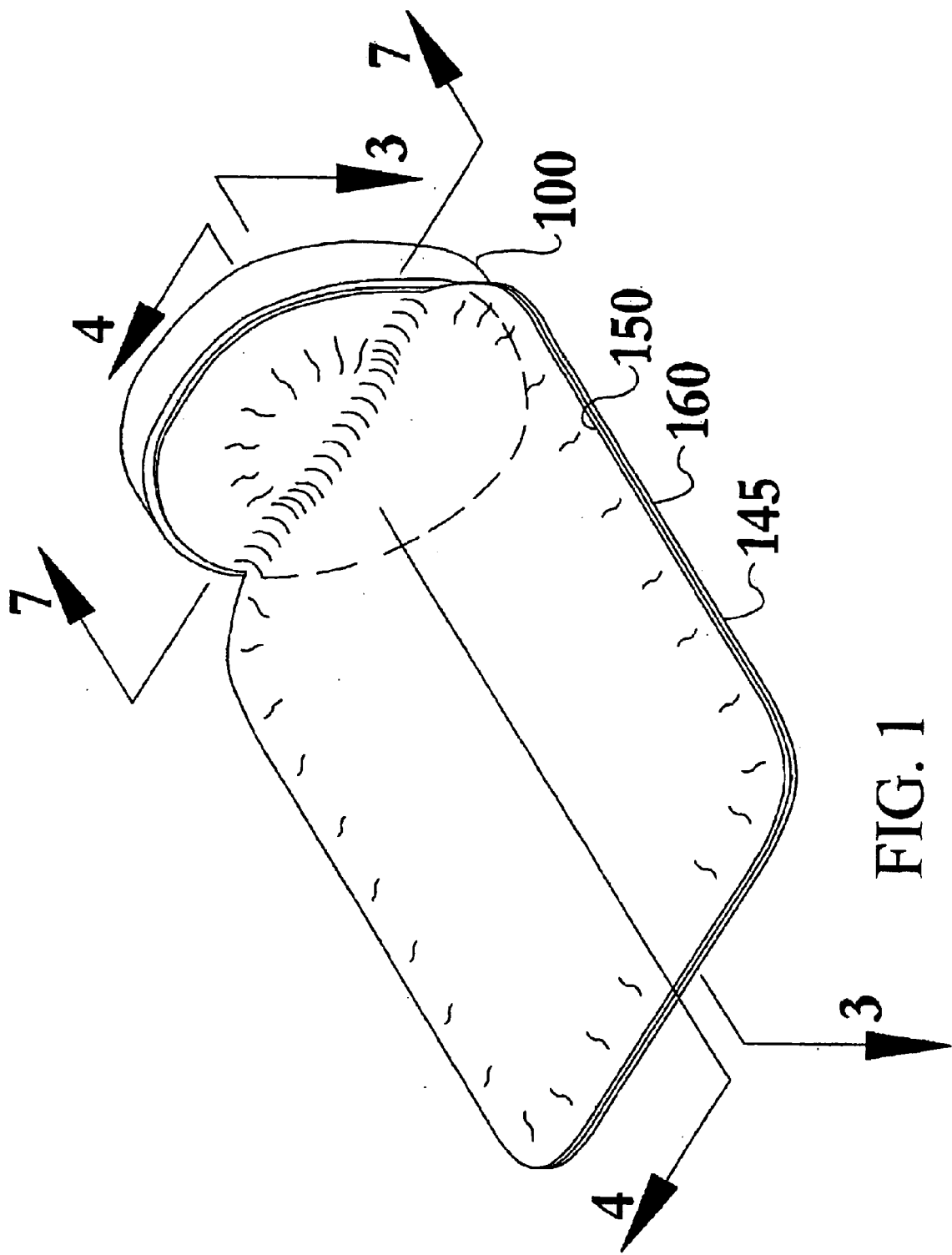
FIG. 1 shows a dispensing and application apparatus in elevated perspective view, in enlarged scale.
Figure 2:
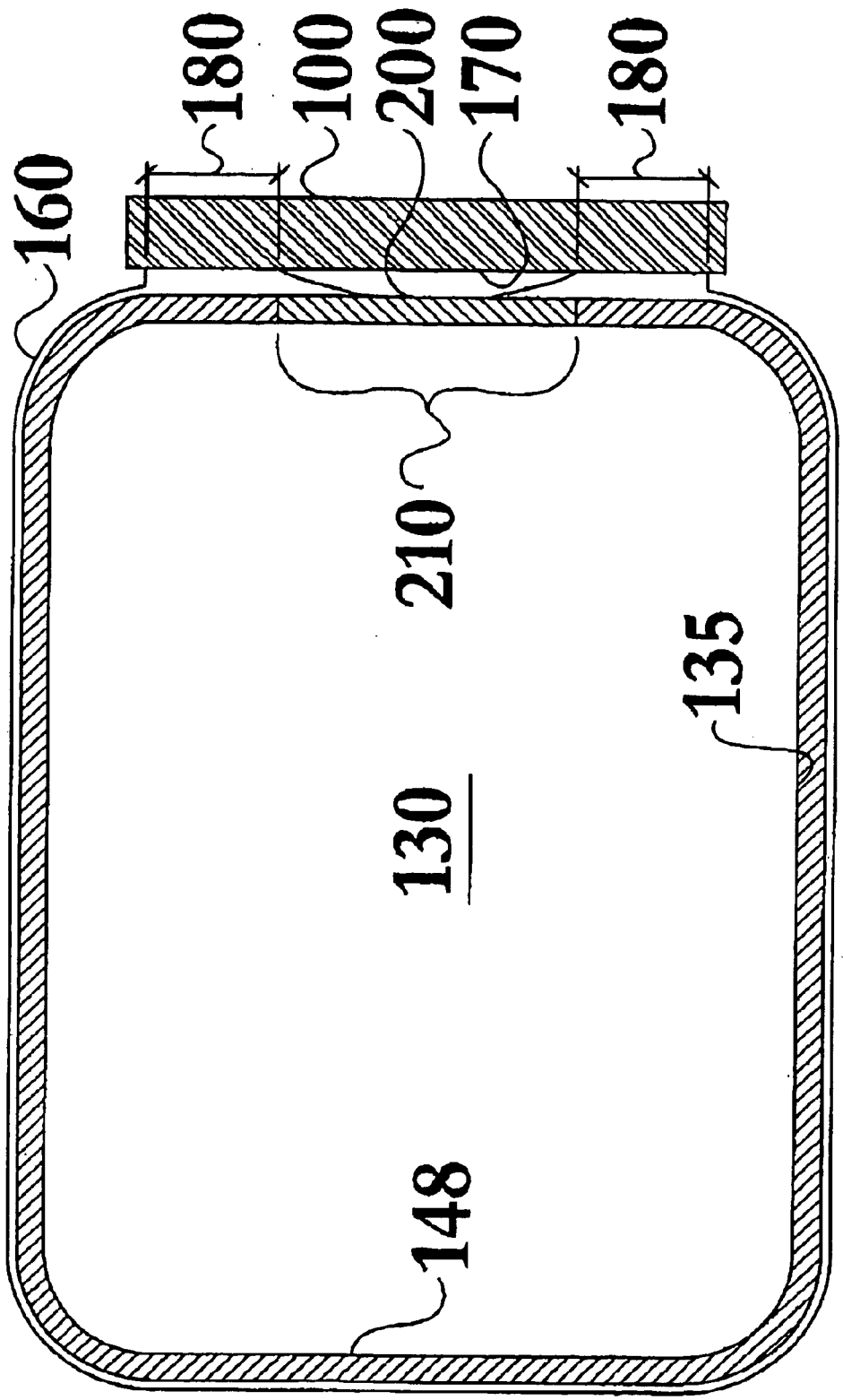
FIG. 2 shows a top plan view of a variation of the second surface (interior) of the inventive apparatus.

The dispensing and application apparatus is designed to contain a flowable substance and to facilitate application of that substance to a surface. Referring generally to FIG. 1, the apparatus in its most general design comprises an applicator or pad 100, a first sheet section 150, and a second sheet section 160. Referring generally to FIG. 2, the inventive apparatus comprises a compartment 130, a chamber 170, and an applicator foam pad 100 and at least one seal 148. The body of the apparatus may be made, as would be apparent to one skilled in the art, of various flexible materials, including in at least one embodiment, a flexible laminated foil material. Other fabrication materials could include, by way of example and not limitation, various plastics, fabrics, non-woven fabrics and coated papers.

The applicator 100 or foam pad can be attached to the film wings with contact or hot-melt adhesives. The applicator may be constructed of porous foam pads, woven or non-woven fabrics or felts. Those of ordinary skill in the art will recognize that various materials can be used for the applicator pad. The applicator 100 and tee film wings may be any desired shape such as square, rectangular, oval, lip shaped and the like with circular being the most preferred. In one embodiment of the present invention, the material used to construct the body of the apparatus, for example the laminated foil material, extends past the applicator pad. The foil extension reduces the possibility that the fingers of the user will come into contact with the dispensed flowable substance or the applicator pad. Further, this flexible foil extension, folds back during use to prevent the bruising of the skin. The foil extension can range from about 1.0 mm to about 50 mm, with about 5 to 25 mm being more preferred, and 5 to 15 mm most preferred.

The foam pads can be a polyurethane foam pad. For example, a 100-pore-inch polyurethane foam pad words well when dispensing liquids of the consistency of hand lotion and the like. Other materials, such as non-woven fabrics, are useful as the applicator pad. One especially useful foam pad is a product from the Jacob Holm Industries of Helen, Ga., known as NORAFIN brand nonwoven spun-laced roll good familiar to whose with skill in the art of medical applicators. NORAFIN is a needle punch composite material comprising 63% lycose, 27% polypropylene and 10% PET.

The material from which the inventive apparatus is constructed can be plastic, fabrics, foils, and the like. One especially useful is a laminated foil product from Pechiney Incorporated. The foil comprises a 48-gauge polyester outside substrate that is heat resistant. The next layer is an adhesive followed by 35-gauge aluminum foil. This works as a moisture and oxygen barrier. Another layer of adhesive is then followed by a 48-gauge layer of polyester. Another layer of adhesive is then followed by a peelable sealant of 2.0 mills. This sealant layer utilizes high-density polyethylene and other polymers to produce the heat-seal. This laminated foil material can have the polyurethane foam or other foam material directly heat-sealed to the peelable sealant layer of the multi-laminate foil. Double-sided contact adhesive can also be used, as well as contact or hot-melt adhesives. These heat sealable foils and laminates are known to those skilled in the art and are commercially available.

Figure 12:
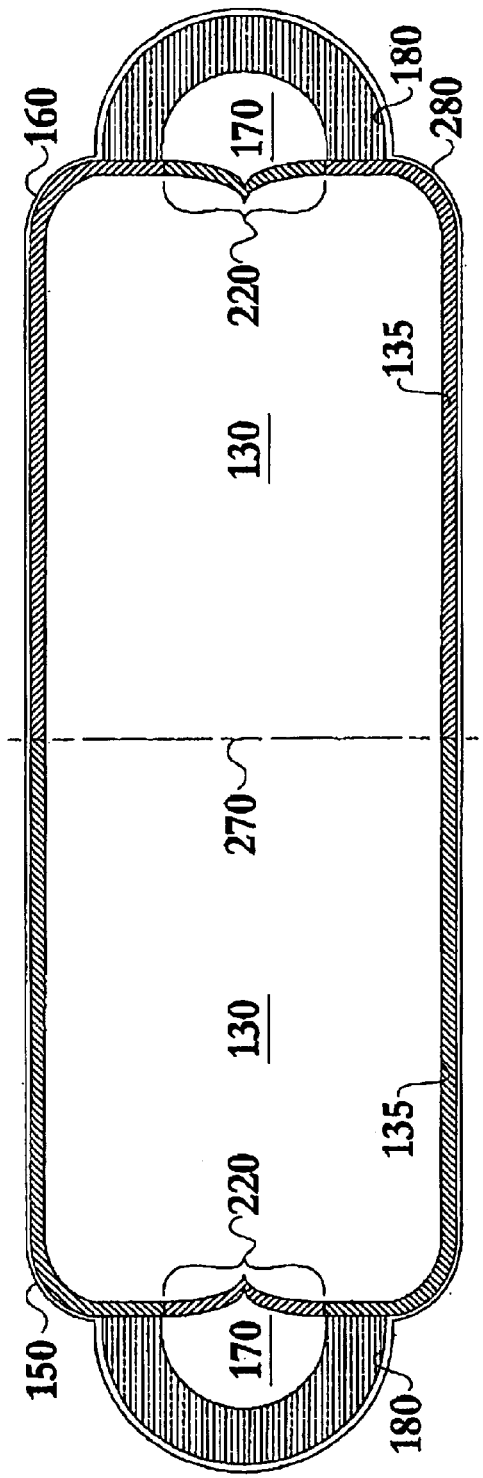
FIG. 12 shows a top plan view of a variation of the first and second sheet member of a single sheet embodiment, opened along a fold line and flattened out to a single plane, of an apparatus similar to that of FIG. 1.
Figure 13:
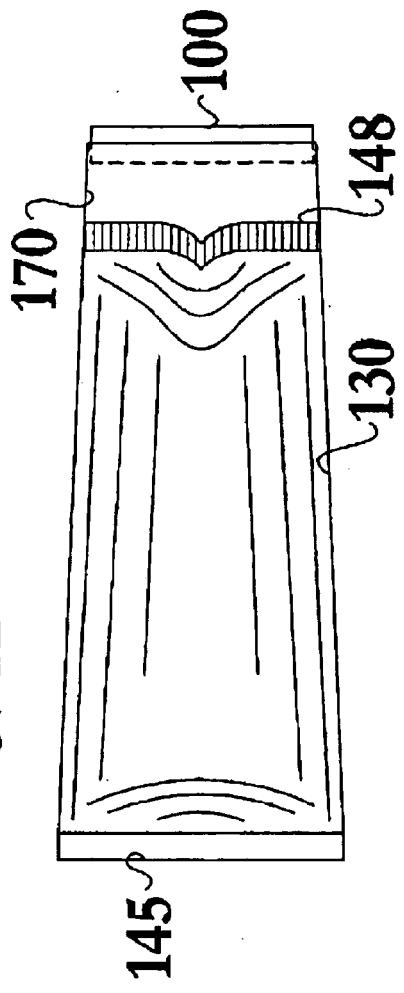
FIG. 13 shows a top plan view of the dispensing apparatus wherein the at least one sheet is configured as a tube.

The compartment 130 may be formed in part by at least one sheet 145 divided by at least one seal 148 to form the compartment. Alternatively, the compartment 130 can be formed with a first sheet section 150 and a second sheet section 160 interconnected with a primary seal 135, as shown in FIGS. 2 and 4. Among other variations, the first sheet section 150 and second sheet section 160 can be formed from a single sheet 280 (See FIG. 12) by folding the sheet 280 along a fold line 270, whereby the first sheet section 150 and second sheet section 160 are additionally interconnected at the fold line 270. In yet another embodiment, the first sheet section 150 and a second sheet section 160, may be individual sheets, as shown in FIG. 1. In yet another embodiment, as shown in FIG. 13, the at least one sheet 145 may be configured as a tube with at least one seal 148. The design of the compartment is intended to contain a measured amount of the flowable substance, ideally a single, or unit dose amount, under clean, or even sterile, conditions. In the embodiments where a primary seal 135 is used to fabricate the apparatus, the primary seal 135 is designed to reliably contain the flowable substance at normal operating pressures during dispensing, as well as to provide a margin of safety to contain the substance in the event that the apparatus is briefly bumped, dropped, or otherwise transiently exposed to higher pressures.

Figure 5:
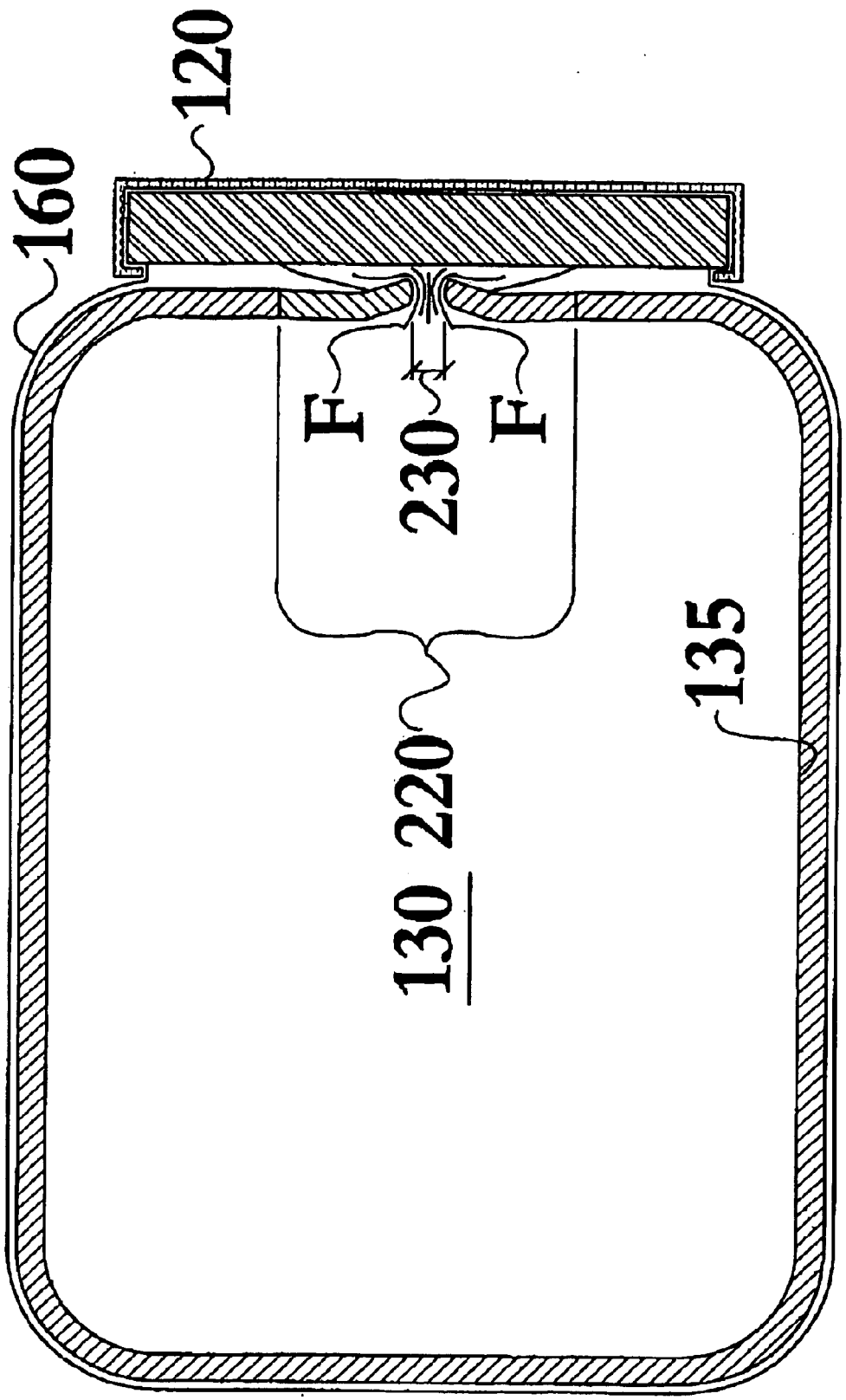
FIG. 5 shows a top plan view of a variation of the second surface of the apparatus shown in FIG. 1.

At least one of the seals 148 is a frangible seal 210 (See FIG. 2) designed to break when exposed to a predetermined pressure, creating a channel 230 (See FIG. 5) permitting fluid communication between the compartment 130 and the chamber 170, as shown by flow indicator lines F in FIG. 5. The frangible seal 210 in FIGS. 2 and 4 are particularly configured to have a lower rupture pressure than the primary seal 135. Additionally, the frangible seal 210 is particularly configured to rupture in a controlled manner across a sufficient area to provide a relatively low-pressure movement of flowable substance into the chamber 170.

Figure 6:
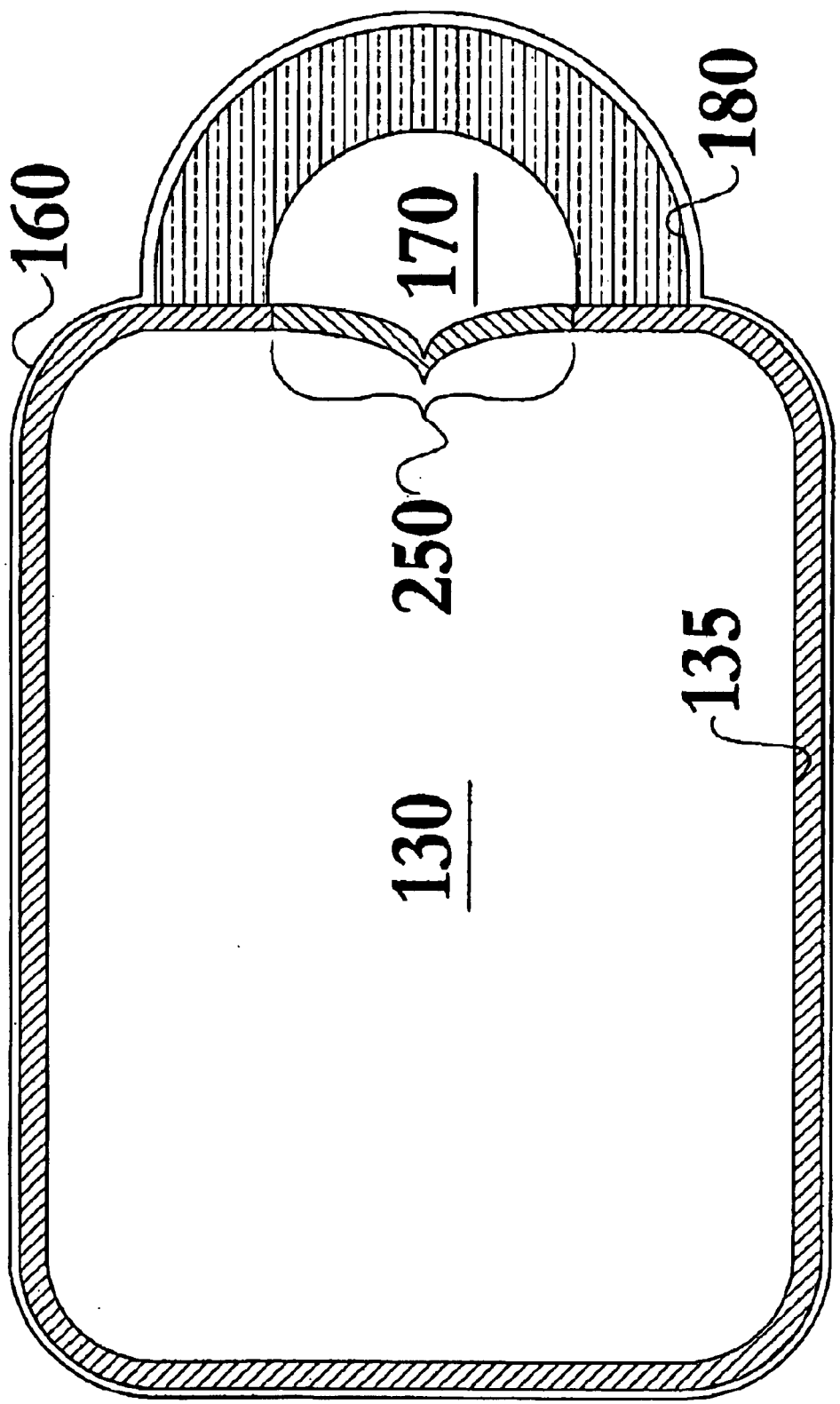
FIG. 6 shows a top plan view of the second surface, flattened out to a single plane, of the apparatus shown in FIG. 3.

This controlled rupture property of the frangible seal 210 is conferred by the design of the seal and the strength of the seal. The frangible seal 210 may have a frangible seal first edge 212 and a frangible seal second edge 214, as indicated in FIG. 9, and multiple conformations are possible for the flungible seal 210, as indicated in FIGS. 2, 3, 8, 9, 10, and 11. In principles that are well known and apparent to those skilled in the art, the provision of an excursion, or excursions, on the surface of, seal, commonly known as stress risers or inflection points 240, see FIGS. 8, 10 and 11, tends to create peel initiation points on the frangible seal 210, at which point or points the frangible seal 210 begins its opening response, or peel, in response to a pressure increase on the side of the frangible seal 210 in which the stress riser or inflection point 240 is oriented. The developing pressure front of a pressure increase against a non-linear barrier, such as that of a frangible seal with stress risers 220 or inflection points 240, is well known to have a region of maximum concentration of pressure in the region of maximum inflection of the frangible seal with stress riser 220, when the inflection point 240 is oriented to extend in the direction of the compartment 130, that is, in the direction of the pressure front. This concentration of force of the pressure front tends to preferentially initiate seal opening, or peel, at the stress riser 220. When pressure is applied to the compartment 130 it begins peeling open the frangible seal 210 starting at the point of the chevron 250, as seen in FIG. 6.

It is not necessary that the stress riser 220 have any particular configuration, only, that the initiation of seal opening, or peel, is enhanced as the inflection point 240 of a stress riser 220 becomes sharper. Thus, a gently curved frangible seal 210 as seen in FIG. 8, would tend to concentrate force at a particular point less intensely than would a frangible seal 210 having an inflection point 240 that resembled a saw tooth, as seen in FIG. 11.

In its simplest construction, and has been shown to be undesirable in some applications as discussed above, the frangible seal 210 may be flat, as seen in FIG. 2, which represents the apparatus as though the first sheet section 150 had been peeled away, leaving the second sheet section 160 exposed for better viewing. In one embodiment of the instant invention, shown in FIG. 8, the frangible seal 210 is formed to have at least one sinusoidal shape. This, as discussed, would be a design that would generally be relatively more difficult to rupture. In another embodiment, the frangible seal 210 further includes a stress riser 220 as seen in FIG. 3. Such a stress riser 220, as discussed, would make the frangible seal 210 generally easier to rupture. A stress riser 220 may, have different configurations in different embodiments, which including, among others, a substantially chevron shape 250, as shown in FIG. 6, which represents the apparatus as though the first sheet section 150 had been peeled away, leaving the second sheet section 160 exposed, with the second sheet section 160 flattened out for better viewing. The chevron shape stress riser 250 may have a sharp inflection point 260 (See FIG. 9) oriented in the direction of the compartment 130.

Additionally, in those embodiments utilizing a frangible seal 210 with a chevron shaped stress riser 250 oriented with the point of maximum inflection 240 of the frangible seal first edge 212 towards the compartment 130, the chevron shape stress riser 250 may have a rear chevron inflection point 260 that does not pass the point of the chamber side of the frangible seal first edge 212. Viewed in another way the maximum orthogonal distance from the rear chevron inflection point 260 to the frangible seal second edge 214 is less than a maximum orthogonal distance between the frangible seal first edge 212 and the frangible seal second edge 214, as shown in FIG. 9. This embodiment has been shown to provide optimal performance in terms of strength and rupture characteristics.

The selection of an optimal design of the stress riser or risers, would lie within the skill of one with ordinary skill in the art, and might be selected to reflect particular characteristics of the flowable substance to be dispensed, including by way of example and not limitation, viscosity of the dispensed substance, desired rupture resistance characteristics of the packaging, type and size of applicator 100, and size of chamber 170. The primary seal 135 and frangible seal 210 may be formed by a variety of techniques, as would be apparent to one skilled in the art, including but not limited to thermal seals, and mechanical or chemical seals. Such mechanical seals could include, by way of example and not limitation, crimping and various retainer clips; and such thermal or chemical seals could include, by way of example and not limitation, adhesive bonds such as chemical adhesive or hot-melt techniques, or other fusion methods.

The materials employed to construct the apparatus of the present invention may be transparent or opaque sheets. Transparent sheets would allow the contents of the container to be visually inspected and to allow the level of the dispensed substance in the container to be visually verified during dispensing. Suitable materials for the fabrication of the device are typically single-layer or multi-layer polymer films.

A discussion of useful films for the construction of the inventive device and the preparation of the various seals can be found in U.S. Pat. No. 6,117,123 to Barney et al.

A severe shortcoming of the prior art, as discussed, has been the lack of a well functioning applicator 100 in dispensing packages. For optimal function, an applicator 100 needs to be absorbent, to facilitate the spreading of dispensed substance within the applicator 100, and to allow the user to apply the dispensed substance easily, and in those applications to the skin, comfortably and cleanly. The instant invention achieves these goals as the apparatus is further configured with an applicator 100, which has a periphery 110 and is joined to the at least one sheet 145 with at least one applicator bond 180, as illustrated in FIGS. 2 and 6. The applicator 100 may be a substantially porous pad, such as a foam pad. The foam pad can be constructed of many natural and synthetic materials. The foam pad should have good reservoiring or holding capacity for the substance being dispensed and fast fluid release for transferring the substance to the skin. Some foams are very absorbent sponges with good liquid retention, but with poor releasing properties. These types of sponges result in a substantial quantity of dispensed substance remaining in the pad, thus wasting the dispensed substance. As seen in FIG. 7, the applicator bond 180 is formed with an interior edge 190 and an exterior edge 200, and in a preferred embodiment, is within the applicator periphery 110. Additionally, the at least one applicator bond 180 may be a chemical and mechanical bond between the applicator 100 and the at least one sheet 145. Such mechanical bonds could include, by way of example and not limitation, crimping and various retainer clips; and such thermal or chemical bonds could include, by way of example and not limitation, adhesive bonds such as chemical adhesive or hot-melt techniques, or other fusion methods.

The embodiment utilizing a configuration wherein the applicator bond 180 lies within the applicator periphery 110, seen in FIG. 7, confers particular advantages on the apparatus. As the applicator bond 180 tends to restrict the flow of the dispensed substance to that area inside the applicator bond interior edge 190, having a portion of the applicator 100 lying outside of the applicator bond area 180 initially provides for an area of dry surface that facilitates an even and comfortable spreading of the dispensed substance. Additionally, this results in a relatively soft edge portion for the applicator 100, which increases comfort levels when the applicator 100 is used to spread a substance on the skin. In an additional embodiment, the foil material may extend beyond the outer edge or periphery of the applicator bond 180. This embodiment protects the user's finger from coming into contact with the dispensed substance or the applicator.

Besides the need for an applicator 100 for optimal dispensing, experiments with various means of attachment of the applicator 100 to a dispensing package indicated that a key design feature necessary to proper function is the provision of a relatively expansive area that may receive the dispensed substance, as it is being dispensed at relatively high pressure through the rupturing frangible seal 210. Such a relatively expandable area allows the dispensed substance to spread out and dissipate the energy it had when passing at a relatively high velocity through the channel 230 and into the chamber 170 (See FIGS. 5 and 6) so it can be gently spread into an applicator. In the absence of such an expandable area, or if the expandable area is too small or otherwise insufficiently expandable, the relatively high pressure dispensing of the substance tends to shoot through or past the applicator 100, without spreading out into the applicator 100. On the other hand, if the expandable area is too large, or otherwise excessively expandable, it is possible for the dispensed substance to achieve such a low-pressure state that it does not adequately spread into the applicator 100.

Accordingly, an optimal design should provide for an easy means of fabricating packages with varying sized expandable areas. The instant invention accomplishes this by its utilization of a chamber 170, and an applicator bond area 180 and applicator 100, and in particular, expandability is imparted to the chamber by the expansion of the chamber 170 walls and by the resilient nature of the applicator 100. This resilient nature allows the contents of the chamber 170 to expand under pressure, thereby absorbing the hydraulic shock as the dispensed substance breaks through the frangible seal 210 and enters the chamber 170. The dispensed substance then tends to remain behind the applicator 100 and can be easily dispensed and spread.

The volume of the chamber 170 may be varied by varying the relative size of the at least one applicator bond area 180 and the applicator 100. In a preferred embodiment, the surface area of the bond area 180 is between approximately 62.5% of the surface area of the applicator 100 and approximately 87.5% of the surface area of the applicator 100. As the ratio of the area of the applicator bond area 180 to the area of the applicator 100, expressed as a percentage, increases towards 100%, the expandability of the chamber 170 decreases and the high pressure effects noted above would become more prominent. As the ratio of the area of the applicator bond area 180 to the area of the applicator 100, expressed as a percentage, decreases towards zero, a point which it cannot reach due to the necessary resulting failure of the bond, the expandability of the chamber 170 increases and the low pressure effects noted above would become more prominent. Numerous embodiments are possible, as would be apparent to one skilled in the art. Varying this applicator bond area 180 to applicator 100 area may be done to reflect particular characteristics of the flowable substance to be dispensed, including by way of example and not limitation, viscosity of the dispensed substance.

The problem associated with "blow-through" of the flowable substance to be dispensed of earlier devices was solved by the discovery that an unattached pad area provided a reservoir to accumulate the volume of cream or other liquid when the frangible seal burst.

Prototype applicators were tested with three different, unattached pad areas. Foam pads for these samples were 1" in diameter and 0.187" thick. Adhesive rings of one inch outside diameter were used to attach the foam pads. The adhesive rings had three different inside diameters: 0.5", 0.375" and 0.25" to evaluate the size of the unattached area on reducing blow-through. Applicators were filled with 0.95 gm of acne cream. These tests showed that prototypes with 0.25" diameter unattached pad area still had some cream blow-through. Prototypes with larger diameter unattached pad area (i.e. 0.5") had no cream blow-through.

The unattached area behind the foam pad provides a flexible reservoir to absorb the liquid volume and hydraulic impact when the frangible seal is broken. Proper design of the reservoir in foam pad specifications can prevent liquid blow-through to the outer surface of the pad. Unsealed area, liquid viscosity and pad specification must each be considered to prevent blow-through.

The width of the bond between the foam pad and the foil wings could be wider at the location where the two foil wings are joined. A wider seal in this area can reduce or eliminate liquid squirting out the small "vee" gap where the foil wings are joined and folded back. A foam pad can be slightly larger than the foil wings to reduce the possibility of the foil contacting and abrading the skin surface.

The cream or liquid is initially dispensed onto the skin from the surface of the foam over the unattached area. The ring of foam that is attached to the foil wings initially has no cream or liquid behind it. This drier outer ring adds to the applicator performance by smoothing and spreading the cream resulting in a thin uniform layer of cream over the skin surface being treated.

The chamber 170 may be formed by the at least one sheet 145, and the applicator 100, and may be bounded in part by the applicator 100, the at least one applicator bond 180, and the frangible seal 210. In an alternate embodiment, the chamber 170 may be additionally bounded in part by one of the at least one seals 148. Alternatively, such as is shown in FIG. 4, in embodiments where the compartment 130 is formed with a first sheet section 150 and a second sheet section 160 interconnected with a primary seal 135, the chamber 170 may be formed by the first sheet section 150, the second sheet section 160, and the applicator 100, and bounded in part by the applicator bond 180, and the frangible seal 210. The chamber 170 may additionally be bounded in part by the primary seal 135.

To protect the contents and to promote cleanliness of the device, the apparatus may include an applicator cover 120 adapted to releasably enclose the applicator, as shown in FIG. 5. Additionally or alternately, as would be apparent to one skilled in the art, the entire apparatus could be enclosed in a suitable packaging to maintain cleanliness, or even in a special use packaging to keep the apparatus sterile. The preferred embodiment of the apparatus is that of a relatively small, hand held device, but there are no particular restrictions on the size of the apparatus or the amount of substance that might be dispensed, other than those general considerations of size, weight, and resultant ease of use.

Industrial Applicability

The apparatus according to the present invention answers a long felt need for a low cost disposable packaging for a wide array of flowable substances, which can include, by way of example and not limitation; pharmaceutical antiseptics, salves, cosmetics, ointments and creams. The apparatus provides a packaging that offers convenience in storage, resistance to package breakage, better sanitation, and lower spillage or waste. Additionally, the apparatus provides a package that allows a user to apply a small measured quantity of a substance in a controlled manner without getting it on the fingers or hands and without the necessity of using the fingers, hands or an additional implement to spread the substance.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations.

Accordingly, even though only few variations of the present invention are described herein, it is to be understood that the practice of such additional modifications and variations and the equivalents thereof, are within the spirit and scope of the invention as defined in the following claims.

We claim:

1. A dispensing and application apparatus wherein the apparatus is designed to contain a flowable substance, comprising:
   a compartment;
   at least one sheet divided by at least one seal, joining the at least one sheet to itself or to another of the at least one sheet, to form the compartment, wherein one of the at least one seal is a frangible seal, wherein the frangible seal further includes a stress riser oriented in the direction of the compartment, designed to break when exposed to a predetermined pressure from the flowable substance, internal to the compartment, created by externally pinching the compartment, where the frangible seal peels apart in such a manner that no portion of the frangible seal separates from the at least one sheet and becomes entrained in the flowable substance, thereby creating a channel permitting fluid communication between the compartment and an expansible chamber;
   an applicator having an applicator surface area, a periphery and being joined to the at least one sheet with at least one applicator bond defining a bond area at the interface between the applicator and the at least one sheet and being characterized by a bond surface area; and
   the expansible chamber being formed by the at least one sheet, and the applicator, and bounded in part by the applicator, the at least one applicator bond, and the frangible seal, such that the expansible chamber absorbs a portion of the kinetic energy of the flowable substance after it breaks through the frangible seal.

2. The apparatus of claim 1, wherein the at least one sheet includes a first sheet section and a second sheet section.

3. The apparatus of claim 2, wherein the first sheet section and the second sheet section are formed from a single sheet by folding the sheet along a fold line.

4. The apparatus of claim 1, wherein the expansible chamber is additionally bounded in part by one of the at least one seal.

5. The apparatus of claim 1, wherein the frangible seal is formed to have at least one sinusoidal shape.

6. The apparatus of claim 1, wherein the stress riser is formed of at least one sharp inflection point.

7. The apparatus of claim 1, wherein the stress riser is formed to be a substantially chevron shape having a sharp inflection point.

8. The apparatus of claim 7, wherein the frangible seal is formed to include a frangible seal first edge and a frangible seal second edge, and the substantially chevron shape has a rear chevron inflection point whereby a maximum orthogonal distance from the rear inflection point to the frangible seal second edge is less than a maximum orthogonal distance between the frangible seal first edge and the frangible seal second edge.

9. The apparatus of claim 1, wherein the stress riser comprises a flat area.

10. The apparatus of claim 9, wherein the at least one applicator bond is a bond selected from chemical bonds and mechanical bonds.

11. The apparatus of claim 1, wherein the applicator is selected from the group consisting of foam pads, wovens, non-wovens and felts.

12. The apparatus of claim 1, wherein the at least one sheet is constructed of flexible laminated foil material.

13. The apparatus of claim 1, wherein the applicator bond exterior edge is within the applicator periphery.

14. The apparatus of claim 1, wherein the surface area of the bond area is between approximately 62.5% of the surface area of the applicator and approximately 87.5% of the surface area of the applicator.

15. The apparatus of claim 1, further including an applicator cover adapted to releasably enclose the applicator.

16. The apparatus of claim 1, wherein the at least one seal and the frangible seal are thermal seals.

17. The apparatus of claim 1, wherein said at least one sheet extends beyond the periphery of said applicator.

18. The apparatus of claim 17, wherein said at least one sheet extends beyond the periphery said applicator from 1 to 50 mm.

19. A dispensing and application apparatus wherein the apparatus is designed to contain a flowable substance, comprising:
   a compartment;
   a first sheet section and a second sheet section interconnected with a primary seal and a frangible seal, wherein the frangible seal further includes a stress riser oriented in the direction of the compartment, to form the compartment, the frangible seal being designed to break when exposed to a predetermined pressure from the flowable substance, internal to the compartment, created by externally pinching the compartment, where the frangible seal peels apart in such a manner that no portion of the frangible seal separates from the at least one sheet and becomes entrained in the flowable substance, thereby creating a channel permitting fluid communication between the compartment and an expansible chamber;
   an applicator having an applicator surface area, a periphery and being joined to the first sheet section and the second sheet section with at least one applicator bond defining a bond area at the interface between the applicator and the first and second sheet sections and being characterized by a bond surface area; and
   the expansible chamber being formed by the first sheet section, the second sheet section, and the applicator, and bounded in part by the applicator, the applicator bond, and the frangible seal, such that the expansible chamber absorbs a portion of the kinetic energy of the flowable substance after it breaks through the frangible seal.

20. The apparatus of claim 19, wherein the first sheet section and the second sheet section are formed from a single sheet by folding the sheet along a fold line, whereby the first sheet section and second sheet section are additionally interconnected at the fold line.

21. The apparatus of claim 19, wherein the expansible chamber is additionally bounded in part by the primary seal.

22. The apparatus of claim 19, wherein the frangible seal is formed to have at least one sinusoidal shape.

23. The apparatus of claim 19, wherein the stress riser is formed to be a substantially chevron shape having a sharp inflection point.

24. The apparatus of claim 23, wherein the frangible seal is formed to include a frangible seal first edge and a frangible seal second edge, and the substantially chevron shape has a rear chevron inflection point whereby a maximum orthogonal distance from the rear inflection point to the frangible seal second edge is less than a maximum orthogonal distance between the frangible seal first edge and the frangible seal second edge.

25. The apparatus of claim 19, wherein the stress riser is formed of at least one sharp inflection point.

26. The apparatus of claim 19, wherein the applicator is selected from the group consisting of porous foam pad, wovens, non-wovens and felt.

27. The apparatus of claim 26, wherein the applicator bond is a chemical and mechanical bond between the applicator and the first and second surfaces.

28. The apparatus of claim 19, wherein the applicator is a foam pad.

29. The apparatus of claim 19, wherein the first sheet section and the second sheet section are sheets of flexible laminated foil material.

30. The apparatus of claim 19, wherein the applicator bond exterior edge is within the applicator periphery.

31. The apparatus of claim 19, the surface area of the bond area is between approximately 62.5% of the surface area of the applicator and approximately 87.5% of the surface area of the applicator.

32. The apparatus of claim 19, further including an applicator cover adapted to releasably enclose the applicator.

33. The apparatus of claim 19, wherein the primary seal and the frangible seat are thermal seals.

34. The apparatus of claim 19, wherein said first and second sheets extend beyond the periphery of said applicator.

35. The apparatus of claim 34, wherein said first and second sheets extends beyond the periphery of said applicator from 1 to 50 mm.

36. A means for dispensing and applying a flowable substance, comprising:
   a means for storing the flowable substance;
   at least one means for establishing a boundary divided by at least one joining means, wherein the at least one joining means joins the at least one boundary establishing means to itself or another of the at least one boundary establishing means, to form the means for storing the flowable substance, wherein one of the at least one joining means is a means for establishing fluid communication between the storing means and a means for expansion when exposed to a predetermined pressure from the flowable substance, internal to the storing means created by externally pinching the storing means, and the fluid communication establishing means does not introduce any portion of itself or the at least one boundary establishing means into the flowable substance;

a means for applying the flowable substance joined to the at least one boundary establishing means with at least one means for bonding; and the expansion means being formed by the at least one boundary establishing means, and the applying means, and bounded in part by the applying means, the at least one bonding means, and the fluid communication establishing means, such that the expansion means absorbs a portion of the kinetic energy of the flowable substance after it.

37. The means for dispensing and applying a flowable substance of claim 36, wherein the at least one boundary establishing means includes a means for establishing a front boundary and a means for establishing a rear boundary.

38. The means for dispensing and applying a flowable substance of claim 36, wherein the expansion means is additionally bounded in part by one of the at least one joining means.

39. The means for dispensing and applying a flowable substance of claim 36, further including a means for covering the applying means.

* * * * *

UNITED STATES PATENT AND TRADEMARK OFFICE
CERTIFICATE OF CORRECTION

PATENT NO. : 6,902,335 B2  Page 1 of 1
APPLICATION NO. : 10/431769
DATED : June 7, 2005
INVENTOR(S) : Bergey et al.

It is certified that error appears in the above-identified patent and that said Letters Patent is hereby corrected as shown below:

Error in name of inventor.

Title Page #75

"Lipoveskaya, Yelena (Howell, MI)" should read as follows:

--Lipovetskaya, Yelena (Howell, MI)--

The letter "T" is missing between the letter "E" and letter "S" of the last name of inventor.

Signed and Sealed this

Tenth Day of July, 2007

JON W. DUDAS
*Director of the United States Patent and Trademark Office*